(12) United States Patent
Han et al.

(10) Patent No.: US 12,251,204 B2
(45) Date of Patent: Mar. 18, 2025

(54) BLOOD PRESSURE MONITORING SYSTEM INCLUDING A LIQUID FILLED SENSOR

(71) Applicant: Apple Inc., Cupertino, CA (US)

(72) Inventors: Caleb C. Han, San Jose, CA (US); Patrick E. O'Brien, Pleasanton, CA (US); Tongbi T. Jiang, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 145 days.

(21) Appl. No.: 17/166,914

(22) Filed: Feb. 3, 2021

(65) Prior Publication Data
US 2022/0240803 A1 Aug. 4, 2022

(51) Int. Cl.
A61B 5/022 (2006.01)
A61B 5/00 (2006.01)
A61B 5/318 (2021.01)

(52) U.S. Cl.
CPC .......... A61B 5/02233 (2013.01); A61B 5/318 (2021.01); A61B 5/681 (2013.01); A61B 2560/0214 (2013.01); A61B 2560/0257 (2013.01); A61B 2562/0247 (2013.01)

(58) Field of Classification Search
None
See application file for complete search history.

(56) References Cited

U.S. PATENT DOCUMENTS

| 4,005,701 A | 2/1977 | Aisenberg et al. |
| 4,290,434 A | 9/1981 | Jewett |
| 4,548,198 A | 10/1985 | Manes |
| 4,896,676 A | 1/1990 | Sasaki |
| 5,135,003 A | 8/1992 | Souma |

(Continued)

FOREIGN PATENT DOCUMENTS

| CN | 103598879 | 2/2014 |
| CN | 104545892 | 4/2015 |

(Continued)

OTHER PUBLICATIONS

Horsey, "YHE smartwatch wearable blood pressure monitor," geeky-gadgets.com/wearable-blood-pressure-monitor-Jul. 2, 2020, Feb. 7, 2020, 3 pages.

Primary Examiner — Aurelie H Tu
(74) Attorney, Agent, or Firm — Brownstein Hyatt Farber Schreck, LLP

(57) ABSTRACT

Embodiments are directed to a blood pressure measurement device that includes a strap configured to couple the blood pressure measurement device to a user, an air pump coupled to the strap and having a housing defining a surface facing the user, and an inflatable chamber positioned on the surface of the air pump and fluidly coupled to the air pump. The inflatable chamber can be positioned between the air pump and the user when the blood pressure measurement device is worn by the user and expand towards the user when inflated. The blood pressure measurement device can also include a pressure sensing chamber coupled to the inflatable chamber and positioned between the inflatable chamber and the user when the blood pressure measurement device is worn by the user. The pressure sensing chamber can include a liquid volume and a pressure sensing device configured to detect a pressure of the liquid volume.

20 Claims, 9 Drawing Sheets

(56) References Cited

U.S. PATENT DOCUMENTS

| | | |
|---|---|---|
| 5,632,278 A | 5/1997 | Rometsch |
| 5,666,404 A | 9/1997 | Ciccotelli et al. |
| 6,162,181 A | 12/2000 | Hynson et al. |
| 6,689,069 B2 | 2/2004 | Bratteli et al. |
| 6,694,821 B2 | 2/2004 | Yamakoshi et al. |
| 6,705,998 B2 | 3/2004 | Stergiopoulos et al. |
| 6,814,077 B1 | 11/2004 | Eistert |
| 7,111,625 B2 | 9/2006 | Jackson |
| 7,678,059 B2 | 3/2010 | Friedman et al. |
| 7,927,283 B2 | 4/2011 | Riobo Aboy |
| 8,690,799 B2 | 4/2014 | Telfort et al. |
| 8,747,328 B2 | 6/2014 | Tichauer |
| 8,911,378 B2 | 12/2014 | Whitaker et al. |
| 8,998,817 B2 | 4/2015 | Pfeiffer et al. |
| 9,192,351 B1 | 11/2015 | Telfort et al. |
| 9,198,584 B2 | 12/2015 | Yamashita et al. |
| 9,986,919 B2 | 6/2018 | Lamego et al. |
| 10,064,561 B2 | 9/2018 | Kinoshita et al. |
| 10,405,806 B2 | 9/2019 | Baik et al. |
| 10,502,328 B2 | 12/2019 | Kotani et al. |
| 10,874,307 B2 | 12/2020 | Narasimhan et al. |
| 11,172,839 B2 | 11/2021 | Ward et al. |
| 11,179,049 B2 | 11/2021 | Niehaus et al. |
| 11,298,032 B2 | 4/2022 | Mou et al. |
| 11,576,583 B2 | 2/2023 | Dana et al. |
| 2002/0002340 A1* | 1/2002 | Nishibayashi ..... A61B 5/02225 600/494 |
| 2004/0044288 A1 | 3/2004 | Gorenberg et al. |
| 2006/0111637 A1 | 5/2006 | Jacober et al. |
| 2007/0185402 A1 | 8/2007 | Yang et al. |
| 2007/0203416 A1 | 8/2007 | Lowe |
| 2009/0012411 A1 | 1/2009 | Lowe et al. |
| 2010/0106029 A1 | 4/2010 | Fraden |
| 2012/0136262 A1 | 5/2012 | Sawanoi et al. |
| 2012/0209129 A1 | 8/2012 | Smith et al. |
| 2013/0060147 A1 | 3/2013 | Welch et al. |
| 2013/0144176 A1 | 6/2013 | Lec |
| 2013/0150736 A1 | 6/2013 | Romano |
| 2014/0187987 A1 | 7/2014 | Fraden et al. |
| 2014/0309541 A1 | 10/2014 | Yamashita et al. |
| 2015/0105675 A1 | 4/2015 | Nakagawa et al. |
| 2016/0038044 A1 | 2/2016 | Banerjee et al. |
| 2016/0106326 A1 | 4/2016 | Bajaj et al. |
| 2016/0120418 A1* | 5/2016 | Oksala ................. A61B 5/0205 600/483 |
| 2016/0255944 A1* | 9/2016 | Baranski ............. A44C 5/2071 |
| 2017/0273579 A1 | 9/2017 | Mori et al. |
| 2017/0290519 A1 | 10/2017 | Zhou |
| 2018/0177411 A1 | 6/2018 | Du et al. |
| 2018/0184920 A1 | 7/2018 | Rabinovich et al. |
| 2018/0310891 A1* | 11/2018 | Fine .................... A61B 5/6838 |
| 2018/0338693 A1 | 11/2018 | Li et al. |
| 2019/0261870 A1 | 8/2019 | Nishikawa |
| 2020/0323446 A1 | 10/2020 | Nishida et al. |
| 2021/0030372 A1 | 2/2021 | Lizio et al. |
| 2021/0059537 A1* | 3/2021 | Nakagawa ............ A61B 5/022 |
| 2021/0127993 A1 | 5/2021 | Matsumura et al. |
| 2021/0169347 A1 | 6/2021 | Ito et al. |
| 2021/0236012 A1 | 8/2021 | Nishida et al. |
| 2021/0251499 A1 | 8/2021 | Ogawa |
| 2021/0285436 A1 | 9/2021 | Fukami et al. |
| 2021/0321889 A1 | 10/2021 | Jain et al. |
| 2022/0000380 A1 | 1/2022 | Li |
| 2022/0015652 A1 | 1/2022 | Lee et al. |
| 2022/0054020 A1 | 2/2022 | Tadele et al. |
| 2022/0087545 A1 | 3/2022 | Jain et al. |
| 2022/0240803 A1 | 8/2022 | Han et al. |
| 2022/0400959 A1 | 12/2022 | Montgomery et al. |
| 2023/0063813 A1 | 3/2023 | Smith et al. |
| 2023/0068620 A1 | 3/2023 | Tadele et al. |

FOREIGN PATENT DOCUMENTS

| | | |
|---|---|---|
| CN | 106037698 | 10/2016 |
| CN | 110099607 | 8/2019 |
| CN | 110301906 | 10/2019 |
| JP | 3120617 U | 3/2006 |
| JP | 3121082 U | 4/2006 |
| JP | 2008178541 | 8/2008 |
| JP | 2020043931 | 3/2020 |
| JP | 2021143647 | 9/2021 |
| KR | 20180033018 | 4/2018 |
| WO | WO 11/023343 | 3/2011 |
| WO | WO 20/016139 | 1/2020 |

* cited by examiner

BLOOD PRESSURE MONITORING SYSTEM INCLUDING A LIQUID FILLED SENSOR

FIELD

The described embodiments relate generally to blood pressure measurement devices, and more particularly, the present embodiments relate to blood pressure measurement devices including a liquid filled sensor.

BACKGROUND

A user may monitor one or more of their physiological parameters by attaching a monitoring device such as a blood pressure monitor to one of their limbs. The blood pressure monitor may include a cuff that secures an inflatable bladder against a limb of the user. The bladder can be inflated to compress the limb, thereby compressing one or more blood vessels in the limb and restricting and/or stopping blood flow through the vessels. The various pressures in the inflated bladder that restrict and/or stop blood flow through the vessels in the limb may be measured and used to determine one or more physiological parameters of a user such as blood pressure of the user. The accuracy of correlating changes in air pressure within the bladder to blood pressures in the arm may vary based on a variety of factors including inflation and deflation rates, the volume of the cuff, and/or the material of the cuff among others. It may be desirable to reduce some of these variations and/or increase the sensitivity of the pressure measurements to help increase the accuracy or precision of measurements taken by blood pressure monitors.

SUMMARY

Embodiments are directed to a blood pressure measurement device that includes a strap configured to couple the blood pressure measurement device to a user, an air pump coupled to the strap and having a housing defining a surface facing the user, and an inflatable chamber positioned on the surface of the air pump and fluidly coupled to the air pump. The inflatable chamber can be positioned between the air pump and the user when the blood pressure measurement device is worn by the user, and expand towards the user when inflated. The blood pressure measurement device can also include a pressure sensing chamber coupled to the inflatable chamber and positioned between the inflatable chamber and the user when the blood pressure measurement device is worn by the user. The pressure sensing chamber can include a liquid volume and a pressure sensing device configured to detect a pressure of the liquid volume.

Embodiments are also directed to a blood pressure measurement device that includes a strap configured to at least partially extend around a limb of a user, an air pump coupled to the strap and defining a surface that faces the user when the blood pressure measurement device is worn by the user, and an inflatable chamber positioned on the surface, fluidly coupled to the air pump, and configured to expand towards the user when inflated. The blood pressure measurement device can include a support plate coupled to the inflatable chamber, positioned between the user and the inflatable chamber when the blood pressure measurement device is worn by the user, and configured to move toward the user when the inflatable chamber is inflated. The blood pressure measurement device can also include a fluid chamber coupled to the support plate, positioned between the user and the support plate when the blood pressure measurement device is worn by the user, and comprising a pressure sensor configured to measure pressures of liquid within the fluid chamber.

Embodiments further include a device for measuring blood pressure of a user that includes a strap that at least partially extends around a limb of the user, a compression mechanism coupled to the strap, defining a surface that faces the user when the device is worn by the user, and configured to move the surface toward or away from the user, and a support plate coupled to the surface. The device can also include a fluid chamber coupled to the support plate, positioned between the user and the support plate when the device is worn by the user, and comprising a pressure sensor configured to measure pressures of liquid within the fluid chamber that result from blood pressure changes of the user.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
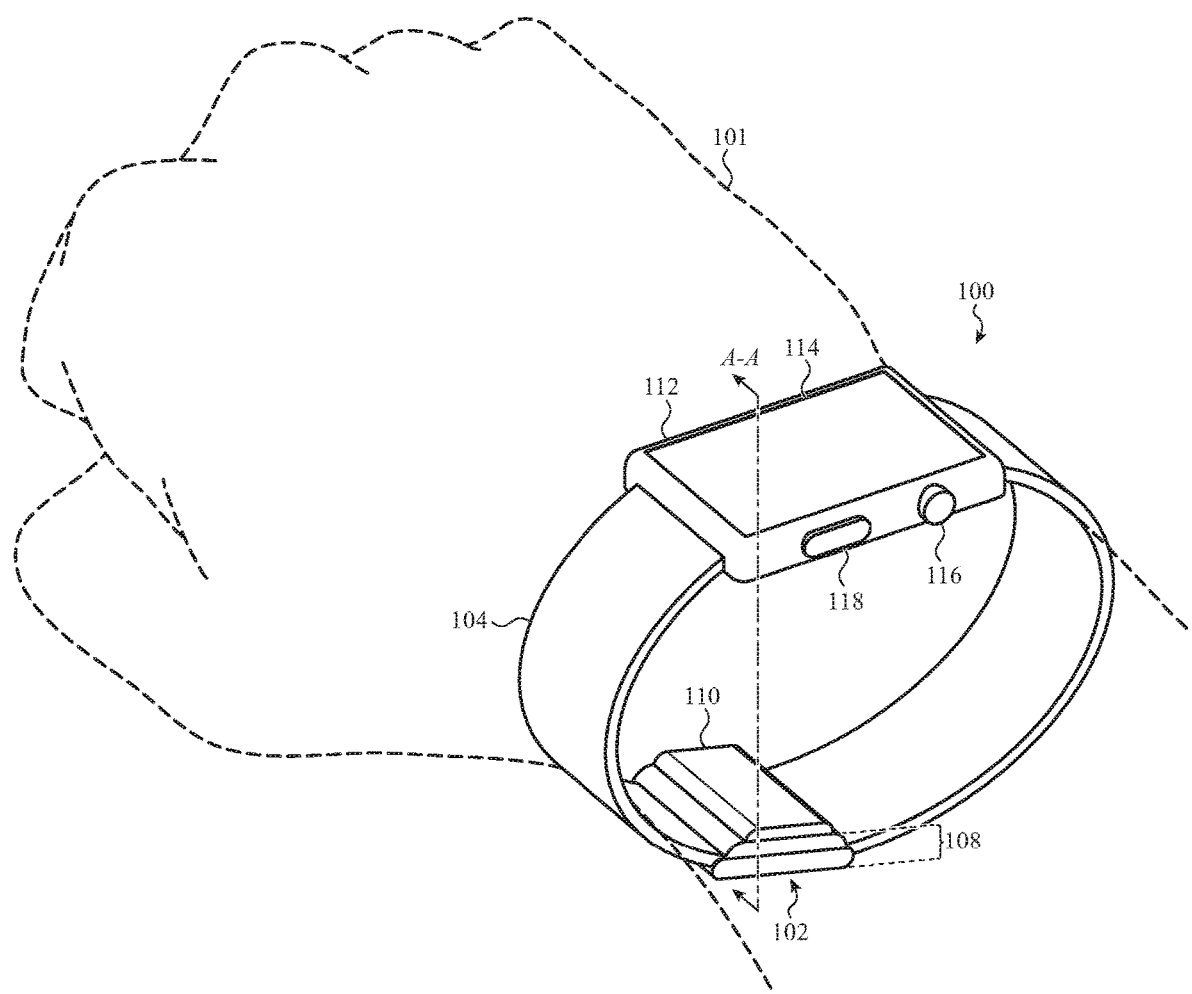
FIG. 1A shows an example blood pressure measurement device being worn by a user.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications and equivalents as can be included within the spirit and scope of the described embodiments as defined by the appended claims.

Embodiments disclosed herein are directed to a blood pressure measurement device that uses a liquid filled pressure sensing chamber to measure blood pressure of a user. The blood pressure measurement device can include a compression system that is separate from the liquid filled pressure sensing chamber and is used to compress the liquid filled pressure sensing chamber against the skin of the user to measure the user's blood pressure. The liquid filled pressure sensing chamber may be more sensitive to pressure changes in the blood vessel as compared to conventional air filled pressure sensing chambers due to the incompressible nature of liquid. Further, having the pressure sensing system separated from the inflation system may help reduce noise and/or increase accuracy of blood pressure measurements as compared to typical blood pressure measurement systems in which a single inflatable cuff is used to both compress a user's arm and measure air pressure in the cuff to estimate blood pressure.

In some embodiments, the blood pressure measurement device is implemented as a pressure sensing stack that includes a liquid filled pressure sensing chamber positioned on an inflatable chamber. A strap can secure the stack against a skin surface of a user such that the pressure sensing chamber is positioned between the inflatable chamber and the user. The inflatable chamber can be inflated to expand towards the user thereby pressing the pressure sensing chamber against the user's skin surface. The pressure sensing chamber can measure blood pressure of the user during the inflation and/or deflation of the inflatable chamber. The pressure sensor can include a flexible housing that contains a volume of liquid, and a pressure sensor that is configured to detect a pressure of the liquid volume. In some cases, the stack structure of the pressure sensing device can help decrease the size of the blood pressure measurement device such that it can be integrated into smaller devices while achieving desirable accuracy and reliability.

The blood pressure measurement device can also include an air pump that is configured to inflate the inflatable chamber. The air pump can be integrated into the pressure sensing stack structure of the pressure sensing device. For example, the inflatable chamber can be positioned on an upper surface of the air pump such that when the blood pressure measurement device is worn by the user the stack includes the air pump positioned furthers from the user, the inflatable chamber positioned between the air pump and the user, and the pressure sensing chamber positioned between the inflatable chamber and the user. The strap can secure the pressure sensing stack to the user such that as the inflatable chamber is inflated it expands primarily towards the user.

In some implementations, the blood pressure measurement device includes a support plate that is positioned between the expansion chamber and the pressure sensing chamber. The support plate can be a rigid or semi-rigid structure that helps distribute the force generated by the inflatable chamber across the pressure sensing chamber and can prevent blood pressure pulse signal loss that may occur between the pressure sensing chamber and the inflatable chamber. In some cases, the expansion chamber, the support plate and the pressure sensing chamber can all have similar profiles such that the support plate and/or expansion chamber extend across substantially the entire bottom surface of the pressure sensing chamber.

The blood pressure measurement device can be an independent device that includes a display, dedicated processor, battery, and so on, which can be mounted to or otherwise integrated into the strap. In other cases, the blood pressure measurement device can be integrated to function with a wearable device such as a smartwatch. For example, the pressure sensing stack can be mounted to a smartwatch band and be electrically coupled with the smartwatch. In these cases, the pressure sensing stack could send pressure measurements to the smartwatch and the smartwatch can analyze, display or combine the pressure data with other data that was collected by the smartwatch, which could include ambient pressure, other physiological measurements of a user such as electrocardiograms, temperatures, oxygen saturation, and so on. In some cases, the blood pressure measurement device could utilize components of the smartwatch such as a power sources.

The example of a smartwatch is given as one example of a device that the blood pressure measurement device can be integrated with. However, the blood pressure measurement device can also be configured to detect blood pressure at locations other than the wrist and/or integrated with other devices such as a dedicated display and processing system, a smartphone, other wearable health monitors, portable music players, and the like. For example, the blood pressure measurement device could be mounted to a strap that is configured to wrap around the upper arm, the wrist, and/or other portions of a user to estimate a blood pressure using measurements from one or more of these locations.

In some cases, the blood pressure measurement device can wirelessly communicate with one or more other devices. For example the pressure sensing device could send blood pressure measurement data to a smartphone, tablet, computer, or other connected devices where it can be viewed, analyzed, stored or otherwise accessed by the user or other authorized party.

The blood pressure measurement device can be secured to a user in variety of ways. For example, the blood pressure measurement device can removably couple to a variety of different straps, which can be configured to attach to different body parts of the user. In other cases, the blood pressure measurement device could be integrated into clothing, belts, hats or other items worn by a user. In some cases, the blood pressure measurement device could be placed on a surface and the user could check their blood pressure by pressing a portion of their body against the device to measure their blood pressure.

These and other embodiments are discussed below with reference to FIGS. 1-7. However, those skilled in the art will readily appreciate that the detailed description given herein with respect to these Figures is for explanatory purposes only and should not be construed as limiting.

FIG. 1 shows an example of a blood pressure measurement device 100 being worn on a limb of a user 101. The blood pressure measurement device 100 can include a pressure sensing stack 102, a strap 104 that secures the sensing strap to the user 101, and an electronic device 106.

The blood pressure measurement device 100 can worn around a limb of the user 101 such as around the wrist, upper arm or other portions of the user's arm, around a user's leg, or any other suitable location for measuring a blood pressure of the user 101. When worn by the user 101, the pressure sensing stack 102 can be operated to measure the user's blood pressure.

In some cases, the pressure sensing stack 102 can include an expansion mechanism 108 and a pressure sensing mechanism 110. The expansion mechanism 108 can press the pressure sensing mechanism 110 against a skin surface of a user 101 in the region of a blood vessel to begin collapsing the blood vessel. As the pressure sensing mechanism 110 is pressed against the user 101 it can measure changes in blood pressure of the user. The expansion mechanism 108 can continue to press the pressure sensing mechanism 110 against the user 101 until the blood vessel has become substantially collapsed and blood flow through the blood vessel has been stopped. The expansion mechanism 108, can then release the pressure applied to the user 101 until the blood vessel is no longer collapsed. The blood pressure measurements taken during the expansion and release of the expansion mechanism can be used to determine one or more blood pressure parameters of the a user such as a diastolic blood pressure, a systolic blood pressure, a mean arterial pressure, or combination thereof. In some cases, the blood pressure measurements can be used to determine other blood pressure parameters such as tracking a pulse pressure wave, identifying one or more cardiac conditions such as abnormal heart rhythms, valve defects such as fibrillation, or the like.

In some cases, the strap 104 can be configured to apply a compressive force to the limb of the user to collapse a blood vessel of the user 101 during a blood pressure measurement. For example, the strap 104 can be configured to tighten around the limb to press the pressure sensing mechanism 110 into the skin surface of a user. Pressure from the strap 104 can be in addition to the expansion mechanism 108 or as an alternative to the expansion mechanism 108.

In some cases, the strap 104 can be a passive structure that secures the pressure sensing stack 102 to the user 101. The strap 104 can be formed from polymer materials such as rubbers, silicone materials, thermoset materials, thermoplastic materials, fabrics, metals, ceramics, or any other suitable material or combination of different materials. In some embodiments, the pressure sensing stack 102 can include components such as a battery, a processor, and a wireless communication module that are used to gather and transmit data related to blood pressure measurements taken by the pressure sensing mechanism 110. In these cases, the blood pressure measurement device 100 may not include the electronic device 106, and instead include the pressure sensing stack 102 and the strap 104.

In some cases, the strap 104 can include one or more functional components used by the blood pressure sensing stack 102. For example, the strap 104 can house or couple to a battery, a processor, a wireless communication module, or the like. In these cases, the blood pressure measurement device 100 may not include the separate electronic device106, and instead include the pressure sensing stack 102 and strap 104.

In other cases, the blood pressure measurement device 100 can include the electronic device 106. The electronic device 106 can be coupled to the user by the strap 104. The electronic device 106 can include a housing 112 and a display 114 that contain components such as a battery, processor(s) and memory, and wireless communication modules that are used to operate the pressure sensing stack 102 and analyze and display blood pressure measurement data for the user 101. In some embodiments, the strap 104 can include one or more electrical connections that electrically couple the pressure sensing stack 102 to the electronic device 106. In some embodiments, the electronic device 106 can be a wearable smart device such as a smartwatch.

The display 114 can be positioned under the cover and at least partially within the housing 112. The display 114 may define an output region in which graphical outputs are displayed. Graphical outputs may include graphical user interfaces, user interface elements (e.g., buttons, sliders, etc.), text, lists, photographs, videos, or the like. The display 114 may include a liquid-crystal display (LCD), organic light emitting diode display (OLED), or any other suitable components or display technology. In some cases, the display 114 may output a graphical user interface with one or more graphical objects that display information collected from or derived from the pressure-sensing system. For example, the display 114 may output one or more blood pressure measurement parameters to the user 101.

The display 114 may include or be associated with touch sensors and/or force sensors that extend along the output region of the display and which may use any suitable sensing elements and/or sensing techniques. Using touch sensors, the electronic device 106 may detect touch inputs applied to the cover, including detecting locations of touch inputs, motions of touch inputs (e.g., the speed, direction, or other parameters a gesture applied to the cover can generate), or the like. Using force sensors, the electronic device 106 may detect amounts or magnitudes of force associated with touch events applied to the cover. The touch and/or force sensors may detect various types of user inputs to control or modify the operation of the electronic device 106, including taps, swipes, multiple finger inputs, single- or multiple-finger touch gestures, presses, and the like.

The electronic device 106 may also include one or more user inputs such as a first input 116 having a cap, crown, protruding portion, or component(s) or feature(s) (collectively referred to herein as a "body") positioned along a side surface of the housing 112. At least a portion of the first input 116 (such as the body) may protrude from, or otherwise be located outside, the housing 112, and may define a generally circular shape or circular exterior surface. The exterior surface of the body of the first input 116 may be textured, knurled, grooved, or otherwise have features that may improve the tactile feel of the first input 116 and/or facilitate rotation sensing.

The first input 116 may facilitate a variety of potential interactions. For example, the first input 116 may be rotated by a user (e.g., the crown may receive rotational inputs). Rotational inputs of the first input 116 may zoom, scroll, rotate, or otherwise manipulate a user interface or other object displayed on the display 114 among other possible functions. The first input 116 may also be translated or pressed (e.g., axially) by the user. Translational or axial inputs may select highlighted objects or icons, cause a user interface to return to a previous menu or display, or activate or deactivate functions among other possible functions. In some cases, the electronic device 106 may sense touch inputs or gestures applied to the first input 116, such as a finger sliding along the body of the first input 116 (which may occur when first input 116 is configured to not rotate) or a finger touching the body of the first input 116. In such cases, sliding gestures may cause operations similar to the rotational inputs, and touches on a cap or crown may cause operations similar to the translational inputs. As used herein, rotational inputs include both rotational movements of the first input 116, as well as sliding inputs that are produced when a user slides a finger or object along the surface of a crown in a manner that resembles a rotation (e.g., where the crown is fixed and/or does not freely rotate). In some embodiments, rotating, translating, or otherwise moving the first input 116 initiates a blood pressure measurement by a pressure sensing stack 102. In some cases, selecting an activity, requesting a location, specific movements of the user, and so on may also initiate pressure measurements by the pressures sensing stack 102.

The electronic device 106 may also include other inputs, switches, buttons, or the like. For example, the electronic device 106 includes a button 118. The button 118 may be a movable button or a touch-sensitive region of the housing 112. The button 118 may control various aspects of the electronic device 106. For example, the button 118 may be used to select icons, items, or other objects displayed on the display 114, to activate or deactivate functions (e.g., to silence an alarm or alert), or the like.

Figure 1B:
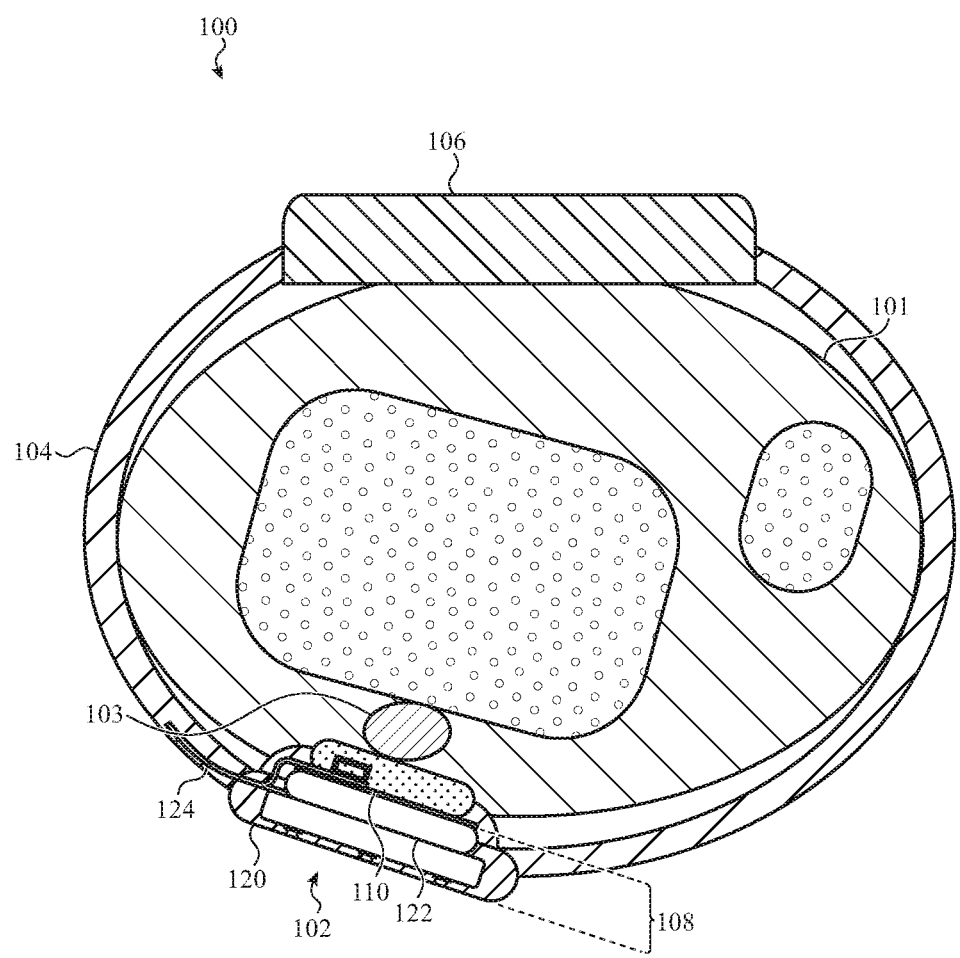
FIG. 1B shows a cross-sectional view of an example blood pressure measurement device being worn by a user.

FIG. 1B shows a cross-sectional view taken along section A-A shown in FIG. 1A of an example blood pressure measurement device 100 being worn by a user 101. The blood pressure measurement device 100 can be operated to measure the blood pressure in a blood vessel 103 of a user 101. The pressure sensing stack 102 can be configured such that the pressure sensing mechanism 110 is positioned between the expansion mechanism 108 and the user 101.

The expansion mechanism 108 can be configured to press the pressure sensing mechanism 110 against the user 101 to collapse the blood vessel 103. In some cases, the expansion mechanism 108 can include an air pump 120 and an inflatable chamber 122 that is fluidly coupled to the air pump 120. As used herein the term "fluidly coupled" is used to describe components that can exchange air using one or more sealed passages. The air pump 120 can be attached to the strap 104 and can form a rigid structure such that as the inflatable chamber 122 is filled with air, it primarily expands towards the user. Accordingly, expansion of the inflatable chamber 122 pushes the pressure sensing mechanism 110 against the user 101 to collapse the blood vessel 103. In this regard, the strap 104 and air pump 120 can be configured to have sufficient rigidity such that as the inflatable chamber 122 expands, the primary motion of this expansion is toward the user 101.

The expansion mechanism 108 can be implemented in various ways. In some cases, the expansion mechanism 108 can be configured to tighten the strap 104 around the user 101 thereby compressing the pressure sensing mechanism 110 against the skin of the user 101 to collapse the blood vessel. In these cases, the expansion mechanism 108 can tighten the strap 104 using a ratcheting mechanism, a screw-based mechanism, gears, friction, a magnetically-actuating element, a piezoelectric element or other suitable system that tightens the strap around the user 101. In other cases, the expansion mechanism 108 can expand toward the user 101 using a piezoelectric actuator, pneumatic actuator, an electromechanical actuator or combination thereof.

The pressure sensing mechanism 110 can include a sealed chamber that contains a volume of liquid and a pressure sensing device that is configured to detect pressure changes of the liquid volume. In this regard, as the pressure sensing mechanism 110 is pressed against the user 101, blood pressures within the blood vessel 103 can be transferred to the liquid volume and detected by the pressure sensing device.

The pressure sensing mechanism 110 can output a signal that indicates the pressures sensed by the pressure sensing device. The signal can be transmitted via one or more electrical connections 124, which can include one or more wires, cables or other suitable structure. In some cases, the electrical connection 124 can carry other signals such as control signals to and from the expansion mechanism 108, signals for other sensors located on the pressure sensing stack 102, or any other electrical communication that occurs between the pressure sensing stack 102 and one or more external components such as the electronic device 106 or components coupled to the strap 104.

Figure 2A:
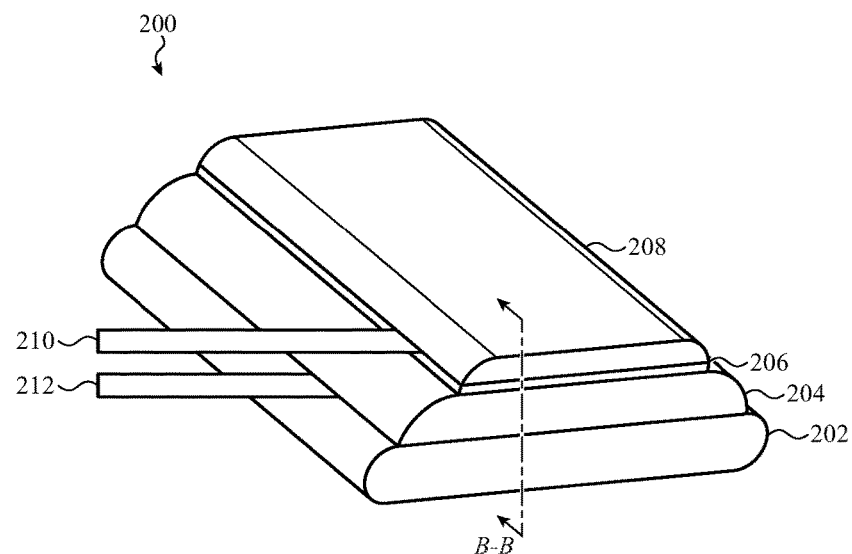
FIG. 2A shows an example pressure sensing stack.

FIG. 2A shows an example pressure sensing stack 200. The pressure sensing stack 200 can include an air pump 202, which can be an example of the air pumps described herein such as air pump 120; an inflatable chamber 204, which can be an example of the inflatable chambers described herein such as inflatable chamber 122; and a pressure sensing chamber 208, which can be an example of the pressure sensing mechanism described herein such as pressure sensing mechanism 110. The pressure sensing stack 200 can include a support plate 206 positioned between the inflatable chamber 204 and the pressure sensing chamber 208. The pressure sensing stack 200 can also include a first electrical connector 210 coupled to the pressure sensing chamber 208, and a second electrical connector 212 coupled to the air pump 202.

Figure 2B:
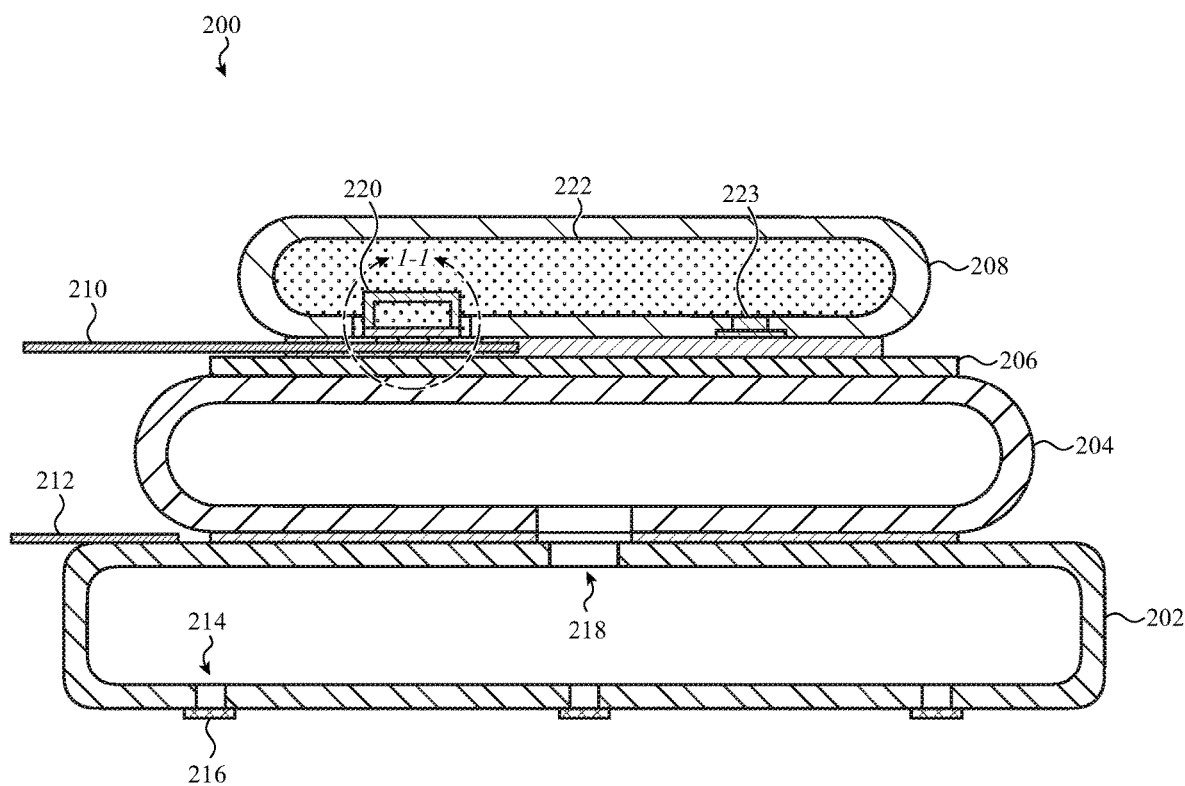
FIG. 2B shows a cross-sectional view of an example blood pressure measurement device.

FIG. 2B shows a cross-sectional view of the pressure sensing stack 200 taken along line B-B shown in FIG. 2A. The air pump 202 can be a piezoelectric air pump, diaphragm air pump, bellow air pump, reciprocating air pump, vane pump, or other suitable pump, or combination thereof. The air pump 202 can have a rigid housing that is attached to a strap of another structure used to secure the sensing stack 200 against a user. In this regard, the air pump 202 can form a rigid base structure that directs expansion of the inflatable chamber 204 toward the user.

In some cases, the air pump 202 can define one or more openings 214 for exchanging air with the external environment, one of which is labeled for simplicity. The openings 214 can be located on a first surface of the air pump 202, which may be referred to as a bottom surface. The air pump 202 can also include one or more membranes 216 that are coupled to the openings 214. The membrane(s) 216 can be configured to prevent water from entering the opening while allowing air to pass into and out of the air pump 202. In some cases, the membrane(s) 216 can be formed from a polytetrafluoroethylene (PTFE) material such as an expanded (ePTFE) material, or other suitable material.

The inflatable chamber 204 can be positioned on a second surface of the air pump 202, which may be referred to as a top surface. The inflatable chamber can be formed from an expandable material such as rubber, silicone elastomer, or polymer compound that can expand at air pressures that are used to collapse a blood vessel of a user. In some cases, a bottom surface of the inflatable chamber 204 can be coupled to the top surface of the air pump 202. The inflatable chamber 204 can be coupled to the air pump 202 in a variety of ways including the use of adhesives, welding, laminating, molding and/or over molding, using mechanical fasteners or other suitable technique, or combinations thereof. The pressure sensor stack 200 can be assembled to define an air passage 218 between the air pump 202 and the inflatable chamber 204. In some cases, the air passage 218 can be on opening, and in other cases the air passage 218 can include a valve, membrane or other structure that controls the direction of air flow between the air pump 202 and the inflatable chamber 204.

The positioning of the bottom surface of the inflatable chamber 204 on the top surface of the air pump 202, can direct the expansion of the inflatable chamber toward a user. For example, a rigidity of the air pump 202 and a strap coupled to the air pump can be configured such that the inflatable chamber 204 primarily compresses the tissue of the user to collapse the blood vessel with little movement of the air pump 202 away from a user.

The support plate 206 can be configured to help distribute the force of the inflatable chamber 204 across the pressure sensing chamber 208 as the inflatable chamber 204 is expanded. Additionally or alternatively, the support plate 206 can prevent blood pressure pulse signal loss between the pressure sensing chamber and the inflatable chamber. The support plate 206 can be formed from a rigid or semi-rigid material that has low deformation at the pressures that are used to compress a blood vessel. For example, the support plate 206 can be formed from a metal, plastic, ceramic, or other suitable material. In some cases, the support plate 206 can be sized to distribute a force created by the inflatable chamber 204 across a bottom surface of the pressure sensing chamber 208. For example, a profile of the top surface of the support plate 206 can be sized to equal or encompass a profile of the bottom surface of the pressure sensing chamber 208. The support plate 206 can be coupled to the inflatable chamber 204 and/or the pressure sensing chamber 208 in a variety of ways including the use of adhesives, welding, molding and/or over-molding, using mechanical fasteners, or combinations thereof.

The pressure sensing chamber 208 can include a flexible outer housing that contains a liquid 222. The pressure sensing chamber 208 can include a pressure sensing device 220 that is configured to detect the pressure of the liquid 222. In some cases, the pressure sensing device 220 contains liquid that is fluidly connected with the liquid 222 in the pressure sensing chamber 208 such that fluid can move between these components to measure the pressure inside the pressure sensing chamber 208. In some cases, the pressure sensing device 220 can be completely or partially contained within the pressure sensing chamber 208. In either case, the first electrical connector 210 can be configured to communicably couple the pressure sensing device 220 to one or more other components of the system such as a processor. The liquid 222 can be any suitable liquid such as water or water-based liquids, oil-based liquids such as a hydraulic liquid, or combinations thereof. The pressure sensing chamber 208 can have a liquid plug 223 to fill liquid and seal the pressure sensing chamber 208. In some cases, the plug and/or filling process can be configured to prohibit or remove any air bubbles or gaseous voids inside the pressure sensing chamber 208.

Figure 2C:
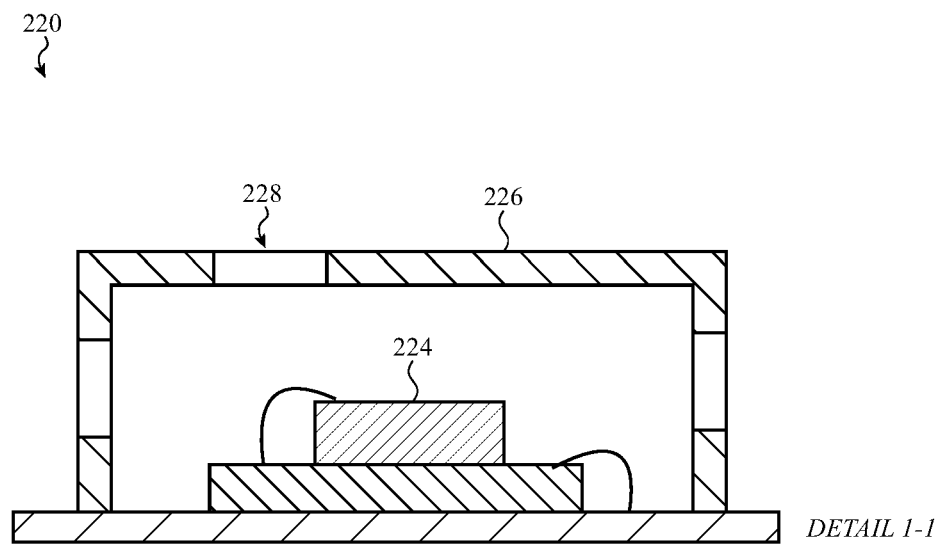
FIG. 2C shows a detailed view of a cross-section of an example pressure sensing device.

FIG. 2C shows detailed view A-A of the pressure sensing device 220 shown in FIG. 2B. The pressure sensing device 220 can include a pressure transducer 224 that is configured to output an electrical signal that is indicative of a pressure of the liquid 222 contained in the pressure sensing chamber 208. The pressure sensing device 220 can also include a cover 226 that defines one or more openings 228. The cover 226 can surround the pressure transducer 224 and can be configured to help prevent air bubbles from forming around the pressure transducer 224, which may occur when the pressure sensing chamber is being filled with the liquid 222.

Figure 3:
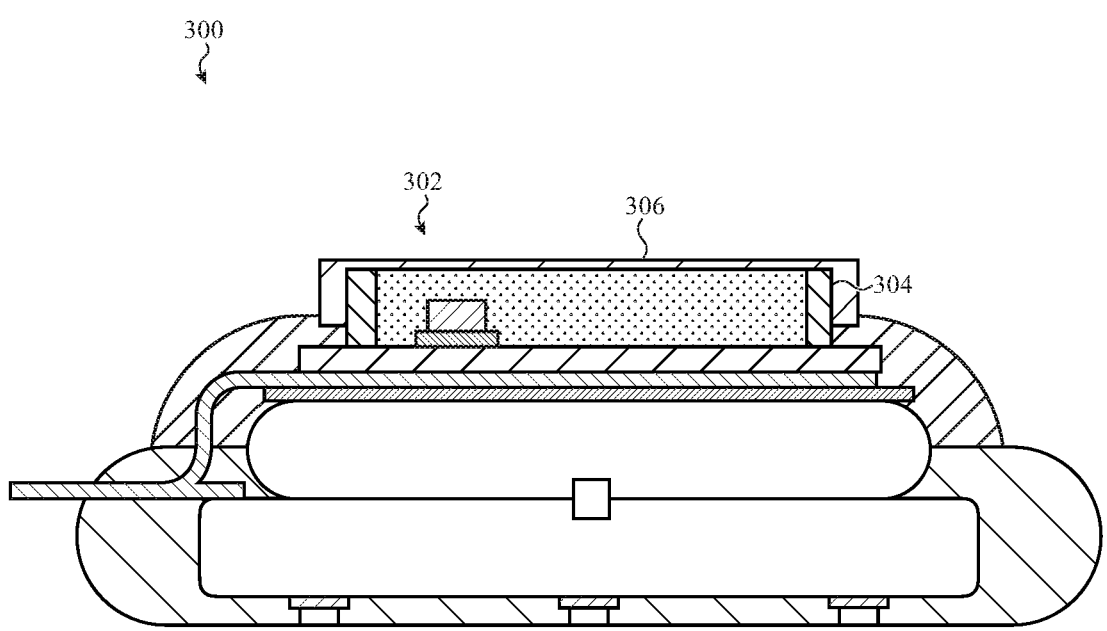
FIG. 3 shows a cross-sectional view of an example blood pressure measurement device.

FIG. 3 shows a cross-sectional view taken along line B-B shown in FIG. 2A of an alternative example of a pressure sensing stack 300. The pressure sensing stack 300 can be an example of the pressure sensing stacks described herein such as pressure sensing stack 102, and 200. The pressure sensing stack 300 shows an alternative example of a pressure sensing chamber 302. The pressure sensing chamber 302 can include a sidewall 304 and a diaphragm 306. The sidewall 304 can be formed from a rigid wall that defines a side structure of the pressure sensing chamber 302. The diaphragm 306 can be formed from a flexible material and positioned over the sidewall to define a top surface of the pressure sensing chamber 302. The diaphragm 306 can contact the skin of a user when the pressure sensing device is worn by a user as described herein. The diaphragm 306 can be attached to the sidewall to form a chamber that contains the liquid.

Figure 4:
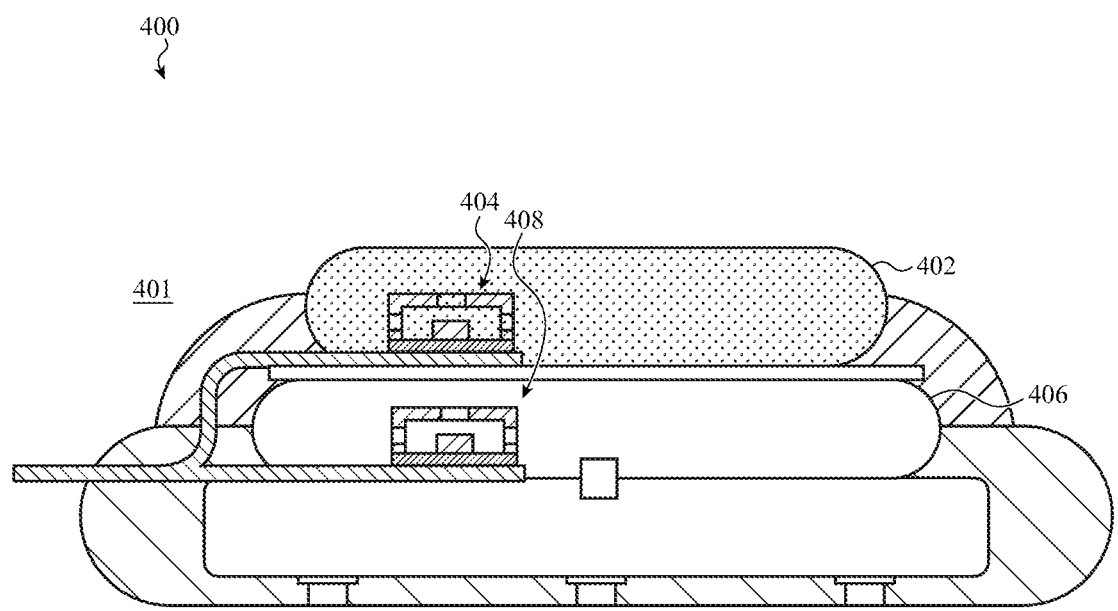
FIG. 4 shows a cross-sectional view of an example blood pressure measurement device.

FIG. 4 shows a cross sectional view taken along line B-B shown in FIG. 2A of an example pressure sensing stack 400. The pressure sensing stack 400 can be an example of the pressure sensing stacks described herein such as pressure sensing stack 102, 200, and 300. The pressure sensing stack 400 shows an example of a differential pressure sensing system that includes two pressure sensing devices. For example, a first pressure sensing device 404 can be configured to measure the liquid pressure in a pressure sensing chamber 402, and a second pressure sensing device 408 can be configured to measure a pressure in an inflatable chamber 406. In some cases, the second pressure sensing device 408 can be used to measure a pressure of the ambient environment 401, such as before and/or after activating an air pump to expand the inflatable chamber 406. In other examples the second pressure sensing device 408 can be located in the air pump, on an external surface of the pressure sensing stack, in the strap, on the electronic device (e.g., electronic device 106), or any other suitable location. Measuring the pressure of the ambient air can be used to determine a blood pressure of the user relative to the ambient air pressure. For example, this can help compensate for elevation changes, or other environmental factors.

In some cases, the second pressure sensing device 408 can measure the pressure in the inflatable chamber 406 during a blood pressure measurement. These air pressures can be used along with the liquid pressures in determining one or more blood pressures of a user. In other cases, pressures measured by the second pressure sensing device 408 can be used to control inflation and deflation of the inflatable chamber 406.

Figure 5A:
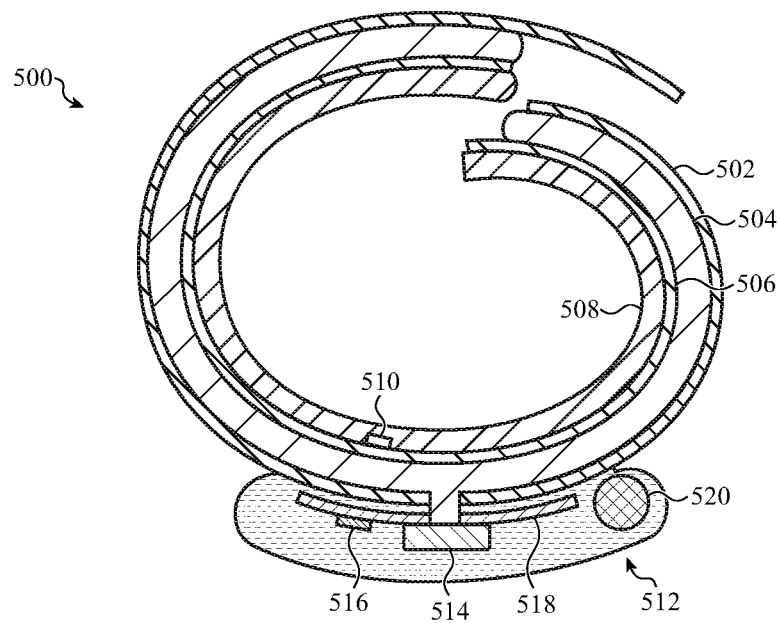
FIGS. 5A and 5B show cross-sectional views of example blood pressure measurement devices.

FIG. 5A is a cross-sectional view of an example blood pressure measurement device 500. The cross-sectional view of FIG. 5A is similar to the view of FIG. 1B. The blood pressure measurement device 500 can include any or all of: a strap 502, which may be any of the straps described herein; an inflatable chamber 504, which may be any of the inflatable chambers described herein; a support plate 506, which may be any of the support plates described herein; a pressure sensing chamber 508, which may be any of the pressure sensing chambers described herein; and a pressure sensing device 510, which may be any of the pressure sensing devices described herein. The blood pressure measurement device 500 can also incorporate any or all of: a control system 512 including an air pump 514, which may be any of the air pumps described herein; an integrated chip 516 (optionally mounted on a circuit board 518 and configured to control operation of the blood pressure measurement device 500); and a battery 520 or other power source.

In the embodiment shown in FIG. 5A, the inflatable chamber 504, the support plate 506 and the pressure sensing chamber 508 extend along the strap 502 such that, when the device is worn by a user, these components substantially encircle an entirety of the user's limb. The strap 502 can be coupled together at opposite ends to secure the blood pressure measurement device 500 to the user. In these examples, the pressure sensing chamber 508 can fully or substantially encircle the limb of the user, thereby permitting pressure sensing around all (or mostly all) of the limb's circumference. This may increase a sensitivity and/or accuracy of blood pressure measurements taken by the blood pressure measurement device 500. In some cases, having the pressure sensing chamber 508 substantially encircle the limb of a user can allow the device to be positioned in a variety of orientations with respect to the user's limb while performing blood pressure measurements on the user. For example, the blood pressure measurement device 500 can be positioned at different angular orientations around a body part such as by rotating the device while it is being worn by the user. Embodiments of the blood pressure measurement device 500 can be configured to wrap around and/or contact various body parts of a user such as a head, torso, leg, bicep, and so on.

In some embodiments, the support plate 506 can bend around the limb of a user while still being sufficiently rigid to distribute forces along the pressure sensing chamber 508 that are generated by the inflatable chamber 504. For example, the support plate 506 can be formed from a thin and rigid material such a thin metal sheet (e.g., spring steel, nitinol, or the like), plastic or plastic composites such as a woven carbon fiber material, or other suitable material or structure. In some cases, the support plate 506 is formed from multiple segments such as band with multiple discrete links that allow the support plate 506 to conform around a body part. The segments forming the support plate can be made from rigid or semi-rigid materials such as metals, plastics, or other suitable materials.

Figure 5B:
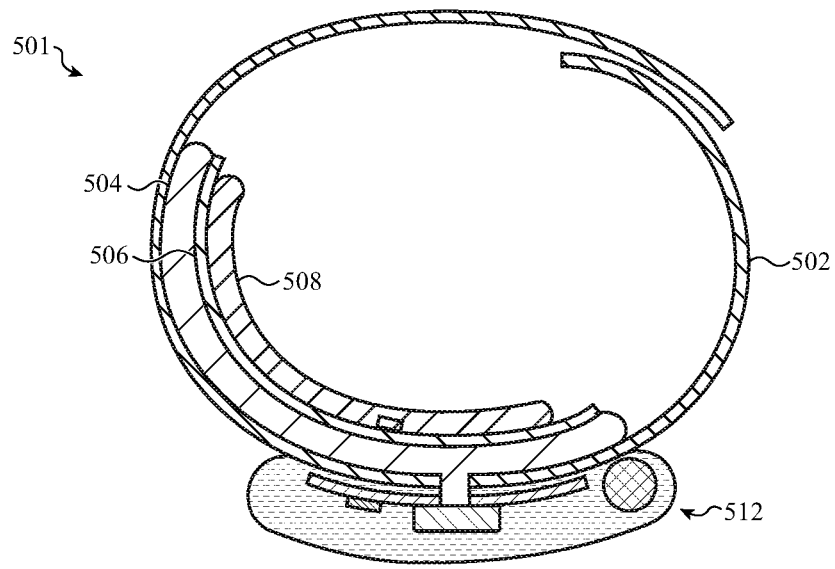

FIG. 5B shows a cross-sectional view of an example blood pressure measurement device 501. The cross-sectional view shown in FIG. 5B is similar to that of FIGS. 5A and 1B. Generally, the blood pressure measurement device 501 may include some or all of the components detailed above with respect to FIG. 5A. In the example shown in FIG. 5B, the inflatable chamber 504, the support plate 506 and the pressure sensing chamber 508 partially surround a limb of the user when the device is worn. In these embodiments, the strap 502 can be longer than a length of the pressure sensing chamber 508, support plate and/or the inflatable chamber, and used to attach the blood pressure measurement device 501 to the user. The blood pressure measurement device 501 may be used on body parts with large circumferences, such as a leg, a bicep, a torso, or the like, where it may be desirable to have the pressure sensing chamber 508 extend partially around the body part. In some cases, the pressure sensing chamber 508, support plate 506, and the inflatable chamber 504 may be positioned on the pressure sensing device 500 such that, when the device is worn by a user, these components are positioned proximate to one or more of the user's blood vessels. For example, the blood pressure measurement device 501 can include features that help position the pressure sensing chamber 508 in a specific orientation relative to a user's limb. For example, the blood pressure measurement device may be rotated around a limb or other body part of a user to orient the pressure sensing chamber 508 relative a blood vessel or other bodily feature. These can include features that interface with a user's anatomy, features that direct a user to wear the device in a specific orientation, and so on. In some cases, the blood pressure measurement device 501 can instruct the user to position or adjust the position of the device to achieve a desired orientation relative to a limb, such as by providing audio instructions, visual instructions such as using a display output, or a combination thereof. In some cases, measurement data from the pressure sensing chamber 508 or other sensors may be used to help direct positioning of the device relative to a limb of a user.

Figure 6:
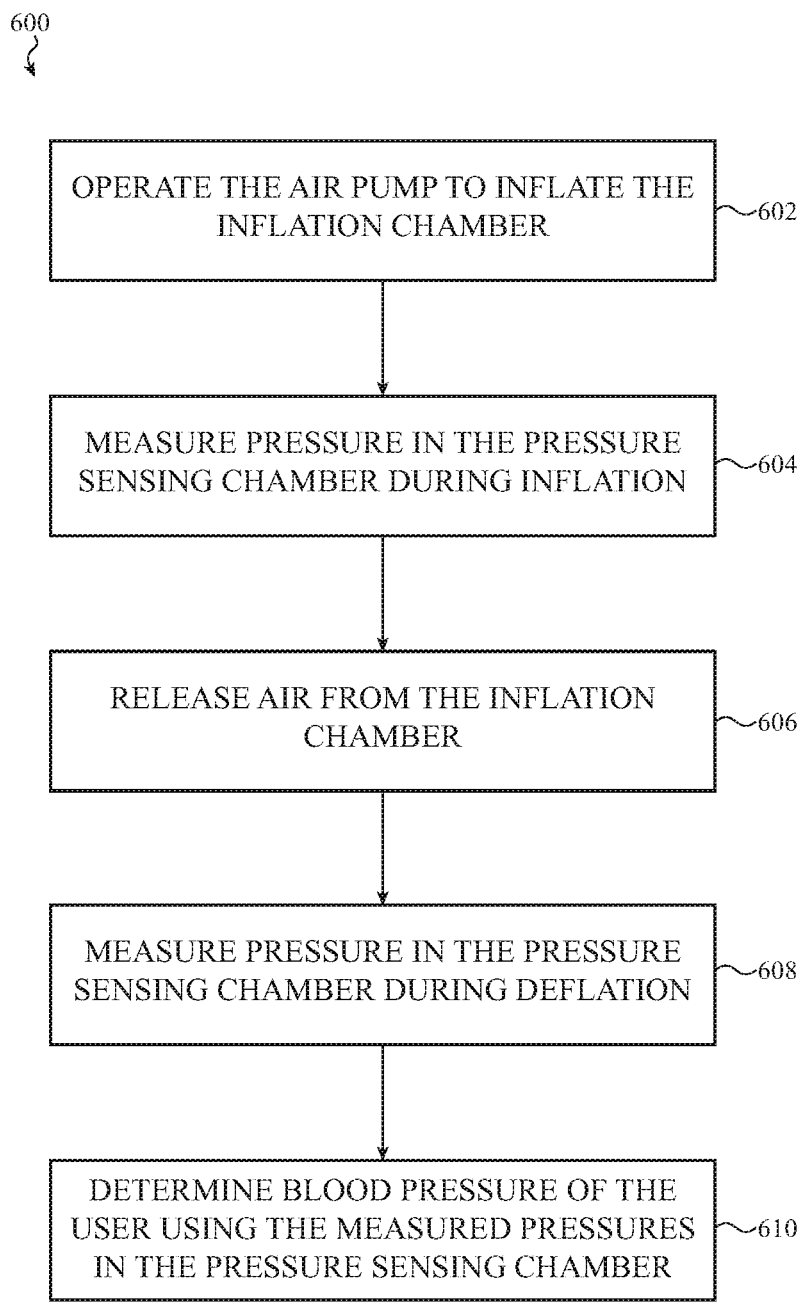
FIG. 6 shows an example process for operating a blood pressure measurement device.

FIG. 6 shows an example process 600 for operating a blood pressure measurement device such as the blood pressure measurement devices described herein.

At 602, the process 600 can include operating the air pump to inflate the inflatable chamber. In some cases, the air pump can inflate the chamber to a defined pressure that is above the pressure that causes collapse of a user's blood vessel. In other cases, pressure measurements from the pressure sensor can be used to control the maximum inflation pressure. In yet other cases, the blood pressure measurement device can include a separate sensor such as a sound sensor that is used to determine collapse of the user blood pressure for controlling the inflation pressure.

At 604, the process 600 can include measuring pressure in the pressure sensing chamber during inflation of the inflatable chamber. As the air pump is operating to inflate the inflatable chamber, the pressure sensing device can be operated to measure blood pressures of a user. In some cases, pressure signal outputs from the pressure sensing device can be used to control an inflation rate, max inflation pressure, or both.

At 606, the process 600 can include releasing the air from the inflation chamber. In some cases, the air release can be controlled by one or more valves coupled to the inflatable chamber. The release rate of air can be controlled via the valve(s). In some cases, pressure signal outputs from the pressure sensing device can be used to control a deflation rate.

At 608, the process 600 can include measuring the pressure in the pressure sensing chamber during deflation of the inflatable chamber. For example, as the inflatable chamber is being deflated, the pressure sensing device can be operated to measure blood pressures of a user.

At 610, the process 600 can include determining a blood pressure of a user using the pressures measured in the pressure sensing chamber during inflation, the pressures measured in the pressure sensing chamber during deflation or a combination thereof. The blood pressure measurements taken during the expansion and release of the expansion mechanism can be used to determine one or more blood pressure parameters of a user such as a diastolic blood pressure, a systolic blood pressure, a mean arterial pressure, or combination thereof. In some cases, the blood pressure measurements can be used to determine other blood pressure parameters such as tracking a pulse pressure wave, identifying one or more cardiac conditions such as abnormal heart rhythms, valve defects such as fibrillation, or the like.

Figure 7:
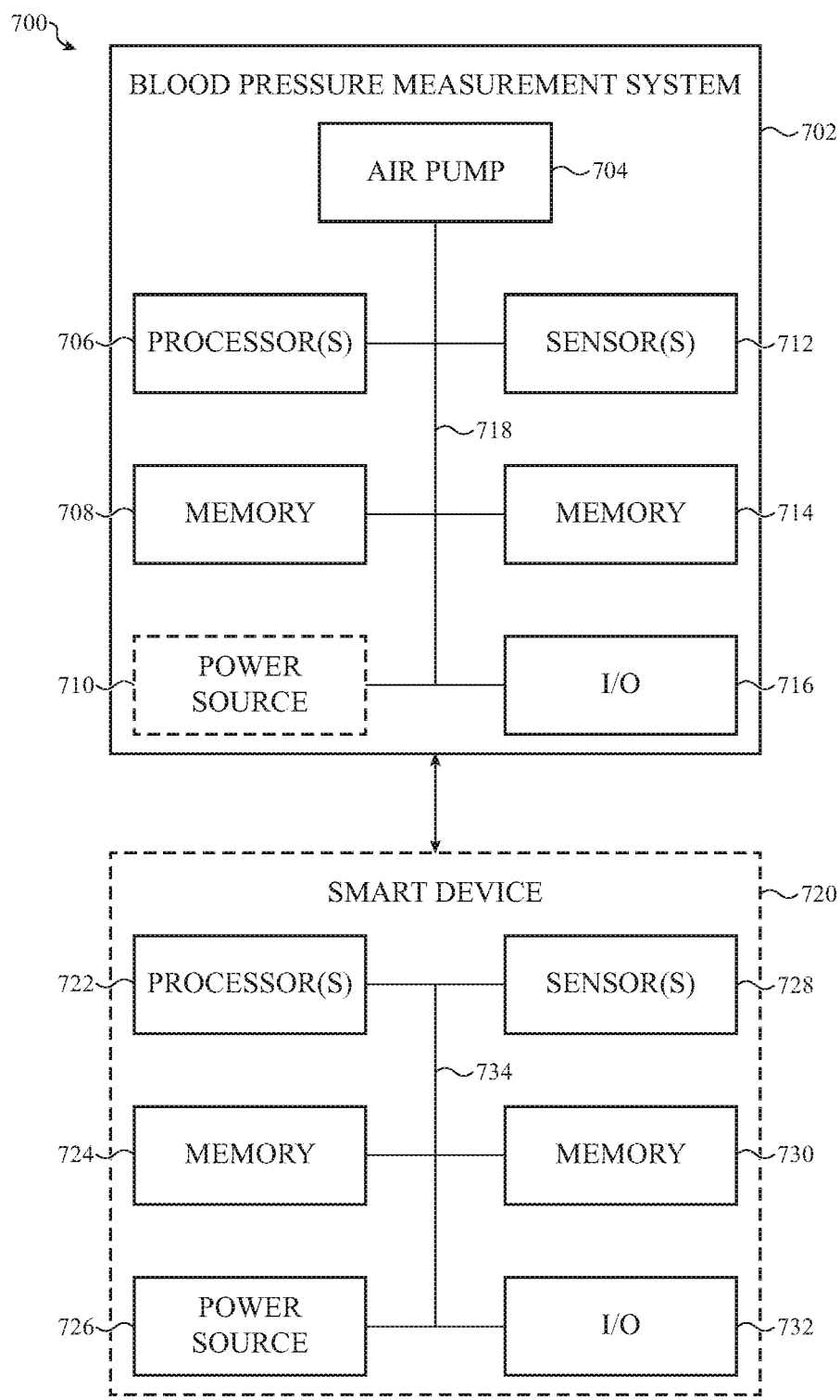
FIG. 7 shows an example system diagram for a blood pressure measurement device.

FIG. 7 shows an example system diagram for a blood pressure measurement system 700, which may in some cases take the form of any of the blood pressure measurement devices or components thereof described with reference to FIGS. 1-6. In some cases, the blood pressure measurement system 700 can include a blood pressure measurement device 702 that is configured to detect one or more blood pressure parameters of a user. For example, the blood pressure measurement device 702 can include components that analyze sensor outputs and display measurement data to a user. In some embodiments, the blood pressure measurement device 702 can interface with a smart device 720 such as a smartwatch, a smartphone, tablet, wearable device such as a health monitoring device, and so on. In these cases, the blood pressure measurement device 702 may utilize components from the smart device 720 for performing blood pressure measurements. For example, the blood pressure measurement device 702 can send outputs from its sensors such as a pressure sensor to the smart device 720, and the smart device 720 can analyze, and display the data to a user.

The blood pressure measurement device 702 can include an air pump 704, a processor 706, memory 708, a power source 710, one or more sensors 712, an input/output (I/O) mechanism 714, and a display 716.

The air pump 704 can be an example of the air pumps described herein and be operable to inflate the inflatable bladder to pressures that collapse a blood vessel of a user. The air pump 704 can be an ultrasonic air pump, diaphragm air pump, bellow air pump, reciprocating air pump, vane pump, or other suitable pump, or combination thereof.

The processor 706 can control some or all of the operations of the blood pressure measurement device 702. The processor 706 can communicate, either directly or indirectly, with some or all of the components of the blood pressure measurement device 702. For example, a system bus or other communication mechanism 718 can provide communication between the air pump 704, processor 706, the memory 708, the power source 710, the sensor(s) 712, the input/output (I/O) mechanism 714, and the display 716.

The processor 706 can be implemented as any electronic device capable of processing, receiving, or transmitting data or instructions. For example, the processor 706 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the blood pressure measurement device 702 can be controlled by multiple processors. For example, select components of the blood pressure measurement device 702 (e.g., a sensor 712) may be controlled by a first processor and other components of the blood pressure measurement device 702 (e.g., the I/O 714) may be controlled by a second processor, where the first and second processors may or may not be in communication with each other.

The memory 708 can store electronic data that can be used by the blood pressure measurement device 702. For example, the memory 708 can store electrical data or content such as, for example, audio and video files, documents and applications, device settings and user preferences, timing signals, control signals, and data structures or databases. The memory 708 can be configured as any type of memory. By way of example only, the memory 708 can be implemented as random access memory, read-only memory, Flash memory, removable memory, other types of memory storage elements, or combinations of such devices.

The power source 710 can be implemented with any device capable of providing energy to the blood pressure measurement device 702. For example, the power source 710 may be one or more batteries or rechargeable batteries. Additionally or alternatively, the power source 710 can be a power connector or power cord that connects the blood pressure measurement device 702 to another power source, such as a wall outlet.

The blood pressure measurement device 702 may also include one or more sensors 712 positioned almost anywhere on the blood pressure measurement device 702. The sensor(s) 712 can be configured to sense one or more type of parameters, such as but not limited to, pressure, sound, light, touch, heat, movement, relative motion, biometric data (e.g., biological parameters), and so on. For example, the sensor(s) 712 may include a pressure sensor, an auditory sensor, a heat sensor, a position sensor, a light or optical sensor, an accelerometer, a pressure transducer, a gyroscope, a magnetometer, a health monitoring sensor, and so on. Additionally, the one or more sensors 712 can utilize any suitable sensing technology, including, but not limited to, capacitive, ultrasonic, resistive, optical, ultrasound, piezoelectric, and thermal sensing technology.

The I/O mechanism 714 can transmit and/or receive data from a user or another electronic device. An I/O mechanism 714 can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The blood pressure measurement device 702 may also include a display 716. The display 716 may include a liquid-crystal display (LCD), organic light-emitting diode (OLED) display, light-emitting diode (LED) display, or the like. If the display 716 is an LCD, the display 716 may also include a backlight component that can be controlled to provide variable levels of display brightness. If the display 716 is an OLED or LED type display, the brightness of the display 716 may be controlled by modifying the electrical signals that are provided to display elements. The display 716 may correspond to any of the displays shown or described herein.

The smart device 720 can include a processor 722, memory 724, a power source 726, one or more sensors 728, an input/output (I/O) mechanism 730, and a display 732.

The processor 722 can control some or all of the operations of the smart device 720. The processor 722 can communicate, either directly or indirectly, with some or all of the components of the smart device 720. For example, a system bus or other communication mechanism 734 can provide communication between the processor 722, the memory 724, the power source 726, the sensor(s) 728, the input/output (I/O) mechanism 730, and the display 732.

The processor 722 can be implemented as any electronic device capable of processing, receiving, or transmitting data or instructions. For example, the processor 722 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the smart device 720 can be controlled by multiple processors. For example, select components of the smart device 720 (e.g., a sensor 728) may be controlled by a first processor and other components of the smart device 720 (e.g., the I/O 730) may be controlled by a second processor, where the first and second processors may or may not be in communication with each other.

The memory 724 can store electronic data that can be used by the smart device 720. For example, the memory 724 can store electrical data or content such as, for example, audio and video files, documents and applications, device settings and user preferences, timing signals, control signals, and data structures or databases. The memory 724 can be configured as any type of memory. By way of example only, the memory 724 can be implemented as random access memory, read-only memory, Flash memory, removable memory, other types of storage elements, or combinations of such devices.

The power source 726 can be implemented with any device capable of providing energy to the smart device 720. For example, the power source 726 may be one or more batteries or rechargeable batteries. Additionally or alternatively, the power source 726 can be a power connector or power cord that connects the smart device 720 to another power source, such as a wall outlet.

The smart device 720 may also include one or more sensors 728 positioned almost anywhere on the smart device 720. The sensor(s) 728 can be configured to sense one or more type of parameters, such as but not limited to, pressure, sound, light, touch, heat, movement, relative motion, biometric data (e.g., biological parameters), and so on. For example, the sensor(s) 728 may include a pressure sensor, an auditory sensor, a heat sensor, a position sensor, a light or optical sensor, an accelerometer, a pressure transducer, a gyroscope, a magnetometer, a health monitoring sensor, and so on. Additionally, the one or more sensors 728 can utilize any suitable sensing technology, including, but not limited to, capacitive, ultrasonic, resistive, optical, ultrasound, piezoelectric, and thermal sensing technology.

The I/O mechanism 730 can transmit and/or receive data from a user or another electronic device. An I/O mechanism 730 can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The smart device 720 may also include a display 732. The display 732 may include a liquid crystal display (LCD), organic light-emitting diode (OLED) display, light-emitting diode (LED) display, or the like. If the display 732 is an LCD, the display 732 may also include a backlight component that can be controlled to provide variable levels of display brightness. If the display 732 is an OLED or LED type display, the brightness of the display 732 may be controlled by modifying the electrical signals that are provided to display elements. The display 732 may correspond to any of the displays shown or described herein.

As described above, one aspect of the present technology is determining physiological parameters of a user such as blood pressure metrics, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A blood pressure measurement device, comprising:
   a strap configured to extend around a first portion of a limb of a user;
   a pressure sensing stack configured to extend along a second portion of the limb of the user, the pressure sensing stack comprising:
      an air pump defining a base of the pressure sensing stack and having a rigid housing defining a surface facing the user, the air pump coupled to the strap and configured to be secured to a user by the strap;
      an inflatable chamber positioned on the surface of the air pump, fluidly coupled to the air pump, and having a first outer profile that is within a profile of the rigid housing, the inflatable chamber configured to:
         be positioned on the rigid housing between the air pump and the user when the blood pressure measurement device is secured to the user; and
         expand towards the user when inflated; and
      a pressure sensing mechanism comprising:
         a sealed chamber containing a volume of liquid, the sealed chamber coupled to the inflatable chamber, positioned between the inflatable chamber and the user when the blood pressure measurement device is worn by the user, and having a second outer profile that is within the profile of the rigid housing; and
         a pressure sensing device positioned within the sealed chamber and configured to detect a pressure of the liquid volume.

2. The blood pressure measurement device of claim 1, wherein:
   the pressure sensing device is a first pressure sensing device; and
   the pressure sensing device further comprises:
      a processor configured to receive a first signal from the first pressure sensing device, the first signal indicative of the detected pressure;
      a support plate positioned between the inflatable chamber and the sealed chamber;
      a second pressure sensing device configured to detect a pressure of an ambient environment; and
      the processor is configured to:
         receive a second signal from the second pressure sensing device indicative of the pressure of the ambient environment; and
         estimate a blood pressure of the user using the first signal and the second signal.

3. The blood pressure measurement device of claim 1, wherein the air pump further comprises:
   an opening; and
   a membrane covering the opening and configured to prevent water from entering the opening, while allowing air to pass through the opening.

4. The blood pressure measurement device of claim 1, further comprising a sensor cover positioned over the pressure sensing device, wherein the sensor cover comprises a first opening and a second opening.

5. The blood pressure measurement device of claim 1, wherein the sealed chamber comprises:
   a rigid wall defining a side structure; and
   a flexible diaphragm positioned over the rigid wall and defining a top surface of the sealed chamber is configured to contact the user when the blood pressure measurement device is worn by the user.

6. The blood pressure measurement device of claim 1, wherein:
   the pressure sensing device is a first pressure sensing device; and
   the blood pressure measurement device further comprises a second pressure sensing device that is configured to detect a pressure of an ambient environment.

7. The blood pressure measurement device of claim 6, wherein the second pressure sensing device is configured to detect the pressure of the ambient environment before activating the air pump, after activating the air pump or before and after activating the air pump.

8. A blood pressure measurement device, comprising:
   a strap configured to at least partially extend around a limb of a user;
   a pressure sensing stack configured to extend along a portion of the limb of the user, the pressure sensing stack comprising:
      an air pump defining a base of the pressure sensing stack and having a rigid housing defining a surface that faces the user when the blood pressure measurement device is worn by the user;
      an inflatable chamber positioned on the surface, fluidly coupled to the air pump, and having a first outer profile that is within a profile of the rigid housing, the inflatable chamber configured to expand towards the user when inflated;
      a support plate coupled to the inflatable chamber, positioned between the user and the inflatable chamber when the blood pressure measurement device is worn by the user, and configured to move toward the user when the inflatable chamber is inflated;
      a pressure sensing mechanism comprising:
         a sealed liquid chamber coupled to the support plate, positioned between the user and the support plate when the blood pressure measurement device is worn by the user, and having a second outer profile that is within the profile of the rigid housing; and
         a pressure sensor poisoned within the sealed liquid chamber and configured to measure pressure of liquid within the sealed liquid chamber.

9. The blood pressure measurement device of claim 8, wherein:
   the blood pressure measurement device further comprises a smartwatch;
   the strap is coupled to the smartwatch and configured to:
      transmit a first signal from the smartwatch and to the air pump to control inflation and deflation of the inflatable chamber;
      transmit a second signal from the pressure sensor to the smartwatch, the second signal indicative of the measured pressures within the sealed liquid chamber; and
   the smartwatch is configured to determine a blood pressure of the user using the first and second signals.

10. The blood pressure measurement device of claim 9, wherein:
the pressure sensor is a first pressure sensor;
the smartwatch further comprises a second pressure sensor configured to measure pressures of an ambient environment; and
the smartwatch is further configured to determine the blood pressure of the user using the measured pressure of the ambient environment.

11. The blood pressure measurement device of claim 9, wherein:
the smartwatch further comprises an electrocardiogram sensor configured to measure an electrical signal of the user; and
the smartwatch is configured to display one or more physiological parameters of the user using the determined blood pressure and the electrical signal.

12. The blood pressure measurement device of claim 8, wherein the strap further comprises:
a battery that is electrically coupled to the air pump; and
a processor configured to:
transmit a first signal to the air pump to control inflation and deflation of the inflatable chamber; and
receive a second signal from the pressure sensor, the second signal indicative of the measured pressures within the liquid chamber.

13. The blood pressure measurement device of claim 8, wherein:
the surface is a first surface;
the air pump defines a second surface that faces away from the user when the blood pressure measurement device is worn by the user;
the first surface defines a first opening for transferring air to or from the inflatable chamber; and
the second surface defines a second opening for transferring air to or from an ambient environment.

14. The blood pressure measurement device of claim 13, further comprising a membrane that prevents water from entering the air pump while allowing air to pass through the second opening.

15. The blood pressure measurement device of claim 8, wherein an outer perimeter of the liquid chamber is positioned within an outer perimeter of the support plate.

16. The blood pressure measurement device of claim 8, wherein the air pump, the inflatable chamber and the sealed liquid chamber are configured to slide along the strap.

17. A device for measuring blood pressure of a user, comprising:
a strap configured to at least partially extend around a limb of the user;
a pressure sensing stack configured to extend along a portion of the limb of the user, the pressure sensing stack comprising:
a compression mechanism coupled to the strap, defining a base of the pressure sensing stack and a surface that faces the user when the device is worn by the user, and configured to move the surface toward or away from the user;
a support plate coupled to the surface;
a pressure sensing mechanism comprising:
a sealed liquid chamber coupled to the support plate, positioned between the user and the support plate when the device is worn by the user, and comprising an outer profile that is within the profile of the support plate; and
a pressure sensor configured to measure pressures of liquid within the sealed liquid chamber that result from blood pressure changes of the user.

18. The device of claim 17, wherein a perimeter of the sealed liquid chamber is contained within a perimeter of the support plate.

19. The device of claim 17, wherein:
the compression mechanism comprises an inflatable chamber that expands towards the user when inflated and when the device is worn by the user; and
the support plate defines a first cross-sectional profile that retains its shape when the inflatable chamber is expanded to compress the limb of the user.

20. The device of claim 19, wherein the sealed liquid chamber comprises a flexible membrane configured to conform to the limb of the user when the inflatable chamber is expanded to compress the limb of the user.

* * * * *